United States Patent [19]

Nobori et al.

[11] Patent Number: 5,942,393
[45] Date of Patent: Aug. 24, 1999

[54] METHOD FOR THE DETECTION OF THE PRESENCE OR ABSENCE OF METHYLTHIOADENOSINE PHOSPHORYLASE (MTASE) IN A CELL SAMPLE BY DETECTION OF THE PRESENCE OR ABSENCE OF MTASE ENCODING NUCLEIC ACID IN THE CELL SAMPLE

[75] Inventors: Tsutomu Nobori; Dennis A. Carson; Kenji Takabayashi, all of San Diego, Calif.

[73] Assignee: The Regents of the University of California, Oakland, Calif.

[21] Appl. No.: 08/772,113

[22] Filed: Dec. 18, 1996

Related U.S. Application Data

[63] Continuation-in-part of application No. 08/176,855, Dec. 29, 1993, abandoned.

[51] Int. Cl.$^6$ .............. C12Q 1/68; C12P 19/34; C12N 15/63; C07H 21/04
[52] U.S. Cl. .......... 435/6; 435/91.2; 435/320.1; 536/23.2; 536/24.31; 536/24.33
[58] Field of Search .......... 435/6, 91.2, 320.1; 536/24.31, 23.2, 24.33, 23.5; 935/77, 78

[56] References Cited

PUBLICATIONS

Nosoh, et al., *Protein Stabilization and Stability Through Protein Engineering*, pp. 62, 143 (1991) Ellis Horwood, N.Y.

Ragione et al., "Enzyme Deficiency and Tumor Suppressor Genes: Absence of 5'–Deoxy–5'–Methylthioadenosine Phosphorylase in Human Tumors", *Adv. Exp. Med. & Biol.*, 348:31–43 (1993).

Ragione et al., "5'–deoxy–5'–methylthioadenosine phosphorylase and p16$^{INK4}$ deficiency in multiple tumor cell lines", *Oncogene*, 10:827–833 (1995).

Nakayama, et al., "Specific Labeling of the Essential Cysteine Residue of Lmethionine γLyase with a Cofactor Analogue, N–(Bromoacetyl) pyridoxamine Phosphate", *Biochemistry*, 27:1587–1591 (1988).

Ragione, et al., "Deficiency of 5–deoxy–5–methylthioadenosine phosphorylase activity in malignancy", *Biochem. J.*, 281:533–538 (1992).

Fitchen, et al., "Methylthioadenosine Phosphorylase Deficiency in Human Leukemias and Solid Tumors", *Cancer Research*, 46:5409–5412 (Oct. 1986).

Kamatani, et al., "Selective killing of human malignant cell lines deficient in methylthiooadenosine phosphorylase, a purine metabolic enzyme", *Proc. Natl. Acad. Sci. USA*, No. 2, 78:1219–1223 (Feb. 1981).

Willi Kreis, et al., "Methionine Dependency of Malignant Tumors", *J. Nat. Cancer Inst.*, No. 83, 10:725 (1991).

Nobori, et al., "Absence of Methythioadenoxine Phosphorylase in Human Gliomas", *Cancer Research*, 51:3193–3197 (Jun. 15, 1991).

Lookwood and Coombs, "Purification and Characterization of methionine γ–lyase from *Trichomonas vaginalis*", *Biochem. J.*, 279:675–682 (1991).

Nobori, et al., "Methylthioadenosine Phosphorylase Deficiency in Human Non–Small Cell Lung Cancers", *Cancer Research*, 53:1098–1101 (Mar. 1, 1993).

Muss, et al., "A phase II trial of peg–L–asparaginase in the treatment of non–hodgkins lymphoma", *Invest. New Drugs*, 8:125–130 (1990).

Willi Kreis, "Tumor Therapy by Deprivation of L–Methionine: Rationale and Results", *Cancer Treatment Rpt.*, No. 6, 63:1069–1072 (1979).

Robert H. Abeles, "A Methionine Salvage Pathway", *Aldrichimica acta*, No. 1, 25:3–7 (1992).

Kries and Hession, "Biological Effects of Enzymatic Deprivation of Lmethionine in Cell Culture and an Experimental Tumor", *Cancer Research*, 33:1866–1869 (Aug. 1973).

Kohsaka & Carson, "Solid–phase Polymerase Chain Reaction", *The Sam & Rose Stein Institute for Research on Ageing*—UCSD Dept. Of Medicine, pp. 1–6 and 2 figures.

Kohsaka, et al., "Microtiter format gene quantification by covalent capture of competitive PCR . . . ", *Nucleic Acids Research*, No. 15, 21:3469–3472 (1993).

Protein Stabilization & Stability Through Protein Engineering, Nosoh et al., 1991 Ellis Horwood, N.Y. pp. 62 and 143.

Ragione et al. (1993) Adv. Exp. Med & Biol. 348: 31–43.

Ragione et al. (1995) Oncogene 10: 827–833.

*Primary Examiner*—Lisa B. Arthur
*Attorney, Agent, or Firm*—Fish & Richardson P.C.

[57] ABSTRACT

A method for the detecting whether methyladenosine phosphatase (MTAse) is present in a cell sample in either a catalytically active or catalytically inactive form. In one respect, the method comprises adding oligonucleotide probes to the sample, which probes are capable of specifically hybridizing to any MTAse encoding nucleic acid in the sample under conditions favoring that hybridization. Absence of MTAse in a sample is considered to be indicative of malignancy. Polynucleotides encoding MTAse, MTAse peptides and antibodies to MTAse, as well as kits for performing the methods of the invention, are provided.

9 Claims, 1 Drawing Sheet

```
   1  TTTATACAGA GCATGACAGT GGGGTCCTCA CTAGGGTCTG TCTGCCACTC
  51  TACATATTTG AAACAGGAGT GGCTTCTCAG AATCCAGTGA ACCTAAATTT
 101  TAGTTTTAGT TGCTCACTGG ACTGGGTTCT AGGAGACCCC CTGTGTTAGT
 151  CTGTGGTCAT TGCTAGGAGA ATCACTTAAT TTTTCTAGA CTCTAGGAGA
 201  AAACAGTTGG TGGTGTACTC ATCACGGGTT AACAATTTCT TCTCTCCTTC
 251  CATAGGCATG GAAGGCAGCA CACCATCATG CCTTCAAGG TCAACTACCA
 301  GGCGAACATC TGGGCTTTGA AGGAAGAGGG CTGTACACAT GTCATGGTGA
 351  CCACAGCTTG TGGCTCCTTG AGGGAGGAGA TTCAGCCCGG CGATATTGTC
 401  ATTATTGATC AGTTCATTGA CANNNNNNNN NNNNNNNNNN GAGGTCGACG
 451  GTATCGATAA GCTTTGTAAA CAATTGTCTT TAGCTTATCC AGAGGAATTG
 501  AGTCTGGAGT AAAGACCCAA ATATTGACCT AGATAAAGTT GACTCACCAG
 551  CCCTCGGAGG ATGGAAAGAT GGCCTTAAAA TAAAACAAAC AAAAACCTTT
 601  TTTGCTTTAT TTGTAGGAC CACTATGAGA CCTCAGTCCT TCTATGATGG
 651  AAGTCATTCT TGTGCCAGAG GAGTGTGCCA TATTCCAATG GCTGAGCCGT
 701  TTTGCCCCAA AACGAGAGAG GTGTGTAGTC TTTCTGGAAG GTGTACCAGA
 751  ATAAATCATG TGGGCTTGGG GTGGCATCTG GCATTTGGTT AATTGGCAGA
 801  CGGAGTGGCC CCATACCCTC ACTCAAGTTT GCTTTGTATT ATGCAAGTTT
 851  ATGGACAGTT ATTTCCTGTT GCTAATAATT TNNNNNNNNN NNNNNNNNNN
 901  AAGTGCAGCC TTAAGTTGTG CATGTGCTAG TATGTTTGA AGTTTCTGGT
 951  TTTCTTTTC TAGGTTCTTA TAGAGACTGC TAAGAAGCTA GGACTCCGGT
1001  GCCACTCAAA GGGGACAATG GTCACAATCG AGGGACCTCG TTTAGCTCC
1051  CGGGCAGAAA GCTTCATGTT CCGCACCTGG GGGCGGATG TTATCAACAT
1101  GACCACAGTT CCAGAGGTGG TTCTTGCTAA GGAGGCTGGA ATTTGTTACG
1151  CAAGTATCGC CATGGCACA GATTATGACT GCTGGAAGGA GCACGACGAA
1201  GCAGTAGGTG GAATTCTTTT CTAAGCACAT ATAGCATGGG TTTCTGGTG
1251  CCAATAGGGT GTCTTAACTG TTTGTTTCTA TTACGTTAGT TTCAGAAAGT
1301  GCCTTTCTAC AAGGTTTTGA AGTTGTTAAT ATTTTCTGTA GTTCCATTGG
1351  AAGGTAAGAA CAAAGATCAA AAGAAAGAAA GAGACACTTT TACCCAAGGA
1401  TCAGTAGTGA AAATAGTACA TTGTAGGCAT GTAGATGTGT TGAGAATCAT
```

FIGURE 1

METHOD FOR THE DETECTION OF THE PRESENCE OR ABSENCE OF METHYLTHIOADENOSINE PHOSPHORYLASE (MTASE) IN A CELL SAMPLE BY DETECTION OF THE PRESENCE OR ABSENCE OF MTASE ENCODING NUCLEIC ACID IN THE CELL SAMPLE

This is a continuation-in-part of application Ser. No. 08/176,855, filed Dec. 29, 1993, now abandoned.

BACKGROUND OF THE INVENTION

1. Field of the Invention

This invention relates to a method to detect methylthioadenosine phosphorylase deficiency in mammalian cells, a condition which is indicative of malignancy in those cells. Detection of cells which are deficient in this enzyme allows those cells to be targeted in chemotherapy to exploit the inability of the cells to convert methylthioadenosine to methionine.

2. History of the Invention

The amino acid methionine (MET) is necessary for the growth of normal and malignant cells. In certain malignant cells this requirement is absolute, i.e., without an adequate supply of MET, the cells die.

In mammalian cells, MET is obtained from three sources. It can be obtained in the diet, or through biochemical synthesis of MET from L-homocysteine (homocysteine) or methylthioadenosine (MTA) (a product of the polyamine biosynthetic pathway). In the latter case, MTA is converted to MET by methylthioadenosine phosphorylase (MTAse; EC 2.4.2.28).

In the past decade, researchers have identified many malignant cell lines which lack MTAse and cannot, therefore, convert MTA to MET. For example, Katamari, et al., Proc. Nat'l Acad. Sci. USA, 78: 1219–1223 (1981) reported that 23% of 3 human malignant tumor cell lines lacked detectable MTAse, while MTAse activity was present in each of 16 non-malignant cell lines studied. MTAse deficiency has also been reported as a characteristic of non-small cell lung cancers (see, Nobori, et al., *Cancer Res.* 53:1098–1101 (1991)), in 6 lines of lymphoma and leukemia cells (id.), in brain tumor cell lines and primary brain tumor tissue samples (id.), and in other malignancies (see, e.g., Kries, et al., *Cancer Res.* 33:1866–1869 (1973), Kries, et al., *Cancer Trmt. Rpts.* 63:1069–1072 (1979), and Rangione, et al., *Biochem. J.* 281:533–538 (1992)). MTAse negative cells principally fulfill their requirement for MET through conversion of homocysteine. However, when homocysteine is not available, the cells will generally die.

L-methionine-L-deamino-y-mercaptomethane lyase (ED 4.4.1.11; METase) is known to degrade not only MET but also homocysteine. Theoretically, therefore, one could starve malignant cells which lack MTAse (i.e., MTAse negative cells) by degrading plasma MET and homocysteine with METase. Normal MTAse positive cells would be expected to fulfill their requirement for MET by the continued conversion of MTA to MET.

One obstacle to the development of a successful approach to MET starvation of malignant cells has been the need to identify which malignancies are suitable targets for the therapy; i.e., which malignancies are MTAse negative. To that end, an assay was developed which predicts whether a malignancy is MTAse negative by determining whether any catalytic activity is present is a cell culture (Seidenfeld, et al., *Biochem. Biophys. Res. Commun.*, 95:1861–1866, 1980). However, because of the commercial unavailability of the radiochemical substrate required for the assay, its use in routine evaluations is not presently feasible. Moreover, the assay does not account for the catalytic lability of MTAse in vitro by detecting whether any of the enzyme is present in the cell culture regardless of whether it is catalytically active at the time that the assay is performed.

This limitation of the activity assay could be avoided by the development of an immunoassay which is sufficiently sensitive to detect relatively minute quantities of enzyme. However, the purification of the MTAse enzyme from natural sources to develop antibodies for use in immunological detection of MTAse has proven to be a laborious process which produces relatively poor yields (Rangione, et al., *J. Biol. Chem,* 261:12324–12329, 1986).

The lack of a simple, efficient means of identifying MTAse deficient cells has contributed in part to the continued unavailability of an effective therapeutic approach to selective in vivo MET starvation of MTAse deficient malignant cells. The present invention addresses this need by providing a method for detection of the presence or absence in a sample of the gene which encodes for MTAse and by providing a recombinant source of MTAse.

SUMMARY OF THE INVENTION

It is the object of the present invention to provide a method for the detection of MTAse deficient cells (which will be considered to be those cells in which the MTAse protein is not detectably present in either a catalytically active or catalytically inactive form). The method of the invention is based on the assumption that MTAse deficiency is due to deletion of the gene which would encode for MTAse from the genome of the mammal which has a MTAse negative malignancy. The method of the invention is therefore directed to the detection of a polynucleotide inside the MTAse protein coding domain of the mammal's genome which, if present, would encode for MTAse but, if absent, would result in the development of MTAse deficient cells.

More specifically, the present invention provides an assay for detecting MTAse which includes the following steps:

(a) obtaining an assayable sample from the malignancy, (b) subjecting the sample to conditions favoring the selective amplification of a nucleic acid which will encode for MTAse, (c) adding oligonucleotide probes which will specifically hybridize to a nucleic acid which will encode for MTAse to the sample under conditions which will allow the probes to detectably hybridize to any such nucleic acid present in the sample, and (d) detecting whether the nucleic acid is present in the sample.

Another aspect of the invention comprises a recombinant MTAse obtained from the expression of MTAse by a suitable vector from a polynucleotide which encodes MTAse. The availability of a recombinant MTAse enables the production of highly pure material with greater ease and in greater quantities than were obtainable using the Rangione method (described supra) for the isolation and purification of native MTAse.

BRIEF DESCRIPTION OF THE DRAWINGS

FIG. 1 maps a partial genomic sequence for the gene or MTAse, and indicates the location of some of the exons in the polynucleotide. Presumed exons are underlined; presumed introns are indicated by one or more "N" substitutions for bases in the polynucleotide sequence. The sequence depicted in FIG. 1 corresponds to the sequence contained in SEQ. ID. No. 1 appended hereto.

DETAILED DESCRIPTION OF THE INVENTION

A. Method for Amplification of Any MTAse Present In a Cell Sample

As noted above, it is an assumption of the invention that MTAse deficiency in cells is the result of the deletion of the gene from a mammal's genome which would normally encode for MTAse. Because the invention is directed toward detecting the presence or absence of this gene in a sample of cells which are suspected of being MTAse negative, nucleic acids in the sample will preferably be amplified to enhance the sensitivity of the detection method. This amplification is preferably accomplished through the use of the polymerase chain reaction (PCR), although the use of a chain reaction in the polymerization step is not absolutely necessary.

For use in the methods of the invention, a biological sample is obtained which is suspected of containing MTAse deficient cells. For example, the sample may comprise body fluid or cells, e.g., from a cell line, tissue or tumor. Such samples are obtained using methods known in the clinical art, e.g. tumor cells may be acquired by biopsy or surgical resection. Preferably, the cells are essentially free from "contaminants"; i.e., cells, proteins and similar components which are likely to falsify the result of the method of the invention. For example, where solid tumors are used as the source for genomic MTAse DNA, normal non-malignant cells and MTAse which may be released from those cells during the procedure performed to obtain the biological sample would be considered to be contaminants.

The nucleic acid to be amplified in the sample will consist of genomic or wild-type DNA which would normally be expected to contain MTAse. This DNA (hereafter the "target DNA") to be amplified is obtainable from a eukaryote, preferably a mammalian organism. Most preferably, the genomic DNA is obtained from a human.

Genomic DNA is isolated according to methods known in the art, e.g., the method described by Maniatis, et al. (Molecular Cloning, A Laboratory Manual, Cold Spring Habor Laboratory, 1982). A working example demonstrating the isolation of a genomic clone of human MTAse is provided herein wherein a cosmid gene library is screened using an MTAse cDNA gene probe which is described further below. However, those skilled in the art will recognize that other suitable means of obtaining the DNA of the invention can be used.

A nucleotide sequence of the genomic clone for MTAse is provided in the Sequence Listing appended hereto as SEQ. ID. No. 1; some of the exons in that sequence are depicted in the map shown in FIG. 1. A strain of *E. Coli* containing the full-length genomic DNA for rat MTAse has been deposited with the American Type Culture Collection, Manassas, Va. by mail before Dec. 29, 1993 and accepted on Dec. 30, 1993 collectively Accession Nos. 55536, 55537, 55538, 55539 and 55540. No admission that this deposit is necessary to enable one to practice the invention is made or intended. The deposit will, however, be maintained in viable form for whatever period is or may be required by the patent laws applicable to this disclosure.

Once the genomic DNA is obtained, the sample containing it is subjected to conditions favoring the selective amplification of the target nucleic acid. Preferably, the target nucleic acid will be a polynucleotide portion of the gene which encodes MTAse (i.e., the "target polynucleotide"). The preferred means of amplifying the target polynucleotide is by PCR. PCR is an in vitro method for the enzymatic synthesis of specific DNA or RNA sequences using oligonucleotide primers that hybridize to specific nucleic acid sequences and flank the region of interest in target nucleic acid. A repetitive series of cycles of template denaturation, primer annealing and enzymatic extension of the annealed primers results in an exponential accumulation of a specific nucleic acid fragment defined at its termini by the 5' ends of the primers. The resulting products (PCR products) synthesized in one cycle act as templates for the next; consequently, the number of target nucleic acid copies approximately doubles in every cycle.

The basic PCR techniques are described in U.S. Pat. No. 4,683,195 and 4,683,202 to Mullis, et al., the disclosures of which are incorporated herein as examples of the conventional techniques for performance of the PCR. However, the invention is not intended to be limited to the use of the PCR techniques which are taught in the '202 patent to Mullis, et al. Since the development of the Mullis, et al. technique, many PCR based assays have been developed which utilize modifications of that technique. These modifications are well-known in the art and will not, therefore, be described in detail here. However, for the purpose of illustrating the scope of the art in this field, several of these modifications are described as follows.

A PCR technique which provides an internal amplification standard using a competitor template which differs from the target nucleic acid in sequence and size is described in *Proc.Natl.Acad.Sci.USA* (1990) 87:2725–2729 (Gilliland, et al., authors). Another technique for performing "competitive" PCR which utilizes templates which differ in sequence but not in size is described in *Nuc. Acids. Res.*, 21:3469–3472, (1993), (Kohsaka, et al., authors). This technique is a particularly preferred technique for its use of enzyme-linked immunoabsorbent assay (ELISA) technology to analyze the amplified nucleic acid(s). A noncompetitive PCR technique which utilizes site-specific oligonucleotides to detect mutations or polymorphisims in genes which may also be applied to the method of the invention is described in *Proc.Natl.Acad.Sci.USA* (1989) 86:6230–6234 (Saiki, et al., authors). Each of these techniques has the advantage of utilizing hybridization probes which assist in eliminating false positive results derived from any nonspecific amplification which may occur during the PCR.

For further background, those skilled in the art may wish to refer to Innis, et al., "Optimization of PCR's", PCR Protocols: A Guide to Methods and Applications (Acad.Press, 1990). This publication summarizes techniques to influence the specificity, fidelity and yield of the desired PCR products.

Oligonucleotide primers (at least one primer pair) are selected which will specifically hybridize to a small stretch of base pairs on either side (i.e., 5' and 3') of the MTAse target polynucleotide (i.e., "flanking sequences"). Those skilled in the art will readily be able to select suitable primers without undue experimentation based on the polynucleotide sequence information set forth in the Sequence Listing appended hereto as SEQ. ID. No. 1 and in FIG. 1.

For primer design, it is important that the primers do not contain complementary bases such that they could hybridize with themselves. To eliminate amplification of any contaminating material which may be present in the sample, primers are preferably designed to span exons (which, for the MTAse gene, are shown in FIG. 1).

As noted above, it may not be necessary to utilize the chain reaction in this polymerization step in order to adequately amplify the nucleic acids in the sample. For example, where the technique described by Kohsaka, et al., supra is utilized so the polymerization step is performed on solid phase support means and is followed by hybridization with target polynucleotide specific probes, the sensitivity of the assay will be such that a single polymerization of the target polynucleotide may be all that is necessary.

Once the amplification step is complete, the PCR products are assayed to determine thereby whether the gene to encode MTAse is present in the sample. Preferably, the double-stranded PCR products will be bound to the solid phase so their strands may be separated by denaturation, thereby allowing sequence-specific probes to hybridize to the bound antisense strand of the PCR product to detect the gene substantially as described in Kohsaka, et al., supra. Alteratively, the PCR products will be removed from the reaction environment and separated from the amplification mixture prior to the addition of probes for hybridization to the double-stranded PCR products. In this latter approach, the PCR products are separated from the amplification mixture according to methods known in the art with regard to the particular method chosen for detection; e.g., by gel exclusion, electrophoresis or affinity chromatography.

Detection of the amplified product may be achieved by using hybridization probes which are stably associated with a detectable label. A label is a substance which can be covalently attached to or firmly associated with a nucleic acid probe which will result in the ability to detect the probe. For example, a level may be a radioisotope, an enzyme substrate or inhibitor, an enzyme, a radiopaque substance (including colloidal metals), a fluorescors, a chemiluminescent molecule, liposomes containing any of the above labels, or a specific binding pair member. A suitable label will not lose the quality responsible for detectability during amplification.

Those skilled in the diagnostic art will be familiar with suitable detectable labels for use in in vitro detection assays. For example, suitable radioisotopes for in vitro use include $^3H$, $^{125}I$, $^{131}I$, $^{32}P$, $^{14}C$, $^{35}S$. Amplified fragments labeled by means of a radioisotope may be detected directly by gamma counter or by densitometry of autoradiographs, by Southern blotting of the amplified fragments combined with densitometry. Examples of suitable chemiluminescent molecules are acridines or luminol. Target sequences hybridized with probes derivatized with acridium ester are protected from hydrolysis by intercalation. Examples of suitable fluorescers are fluorescein, phycobiliprotein, rare earth chelates, dansyl or rhodamine.

Examples of suitable enzyme substrates or inhibitors are compounds which will specifically bind to horseradish peroxidase, glucose oxidase, glucose-6-phosphate dehydrogenase, β-galactosidase, pyruvate kinase or alkaline phosphatase acetylcholinesterase. Examples of radiopaque substance are colloidal gold or magnetic particles.

A specific binding pair comprises two different molecules, wherein one of the molecules has an area on its surface or in a cavity which specifically binds to a particular spatial and polar organization of another molecule. The members of the specific binding pair are often referred to as a ligand and receptor or ligand and anti-ligand. For example, if the receptor is an antibody the ligand is the corresponding antigen. Other specific binding pairs include hormone-receptor pairs, enzyme substrate pairs, biotin-avidin pairs and glycoprotein-receptor pairs. Included are fragments and portions of specific binding pairs which retain binding specificity, such a fragments of immunoglobulins, including Fab fragments and the like. The antibodies can be either monoclonal or polyclonal. If a member of a specific binding pair is used as a label, the preferred separation procedure will involve affinity chromatography.

If no amplified product can be detected in the assay described above, this is indicative of MTAse deficiency in the cells present in the sample. Because normal (i.e., nonmalignant) cells will always be expected to have MTAse present in detectable quantities, the finding of MTAse deficiency indicates that the analyzed genomic DNA was obtained from malignant cells. The assay of the invention is particularly suitable for diagnostic purposes, e.g. for the diagnosis of MTAse deficiency associated with neoplasms, particularly malignant neoplasms.

Where desired, the sample can be prescreened for MTAse catalytic activity using the method described by Seidenfeld, et al., *Biochem. Biophys. Res. Commun.*, 95:1861–1866 (1980); see also, Example I, infra). The inventive assay will then be used to determine whether the gene encoding MTAse is present in cells in the sample. The sample may also be tested for the presence of catalytically active or inactive protein for the purpose of screening out contaminants; i.e., nonmalignant cells in the sample. A suitable immunoassay for use in this regard is described in Nobori, et al., *Cancer Res.* 53:1098–1101 (1991) and in co-pending U.S. patent application Ser. No. 08/176,413, filed on Dec. 29, 1993.

B. Production of Synthetic or Recombinant MTAse Polynucleotides and Peptides

It is another object of the present invention to provide polynucleotides (in particular, oligonucleotides) which enable the amplification of a MTAse specific nucleic acid sequence. The strategy for designing such oligonucleotides will consider the aspects mentioned above. Such oligonucleotides are particularly useful for diagnosis of MTAse deficiency associated with malignancy.

The invention also provides synthetic and recombinant MTAse and MTAse peptides as well as polynucleotides which encode MTAse and MTAse peptides. As used herein, "polynucleotide" refers to a polymer of deoxyribonucleotides or ribonucleotides, in the form of a separate fragment or as a component of a larger construct. DNA encoding MTAse or an MTAse peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code.

Peptides and polynucleotides of the invention include functional derivatives of MTAse, MTAse peptides, and nucleotides encoding therefor. By "functional derivative" is meant the "fragments," "variants," "analogs," or "chemical derivatives" of a molecule. A "fragment" of a molecule, such as any of the polynucleotides of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

A molecule is said to be "substantially similar" to another molecule if the sequence of amino acids in or, in the case of polynucleotides, produced by both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences,* 16th Ed., Mack Publishing Co., Easton, Pa. (1980).

Minor modifications of the MTAse primary amino acid sequence may result in proteins which have substantially equivalent activity as compared to the MTAse enzyme and peptides described herein. Such modifications may be deliberate, as by site-directed mutagenesis, or may be spontaneous. All of the proteins and peptides produced by these modifications are included herein as long as the biological activity of MTAse still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which may not be required for the enzyme to exert the desired catalytic or antigenic activity.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that the antibodies raised to the substituted polypeptide also immunoreact with the unsubstituted polypeptide.

DNA sequences for use in producing MTAse and MTAse peptides of the invention can also be obtained by several methods. For example, the DNA can be isolated using hybridization procedures which are well known in the art. These include, but are not, limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture.

An MTAse containing cDNA library can be screened by injecting the various mRNA derived from cDNAs into oocytes, allowing sufficient time for expression of the cDNA gene products to occur, and testing for the presence of the desired cDNA expression product, for example, by using antibody specific for MTAse or by using probes for the repeat motifs and a tissue expression pattern characteristic of MTAse. Alternatively, a cDNA library can be screened indirectly for MTAse peptides having at least one epitope using antibodies specific for the polypeptides. As described in Section C below, such antibodies can be either polyclonally or monoclonally derived and used to detect expression product indicative of the presence of MTAse cDNA.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The development of specific DNA sequences encoding MTAse or fragments thereof can also be obtained by: 1) isolation of double-stranded DNA sequences from the genomic DNA: 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

On the present invention, the polynucleotide and any variants thereof encoding MTAse may be inserted into a recombinant expression vector. The term "recombinant expression vector" refers to a plasmid, virus or other vehicle known in the art that has been manipulated by insertion or incorporation of the appropriate genetic sequences. Such expression vectors contain a promoter sequence which facilitates the efficient transcription of the inserted genetic sequence of the host.

Transformation of a host cell with recombinant DNA may also be carried out by conventional techniques as are well known to those skilled in the at. Host cells may be eukaryotic (such as Chinese hamster ovary cells) or prokaryotic (such as bacteria or yeast). Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplasm to the host cell or by electroporation.

Isolation and purification of microbially expressed MTAse, or fragments thereof, provided by the invention, may be carried out by those of ordinary skill in the art using conventional means including preparative chromatography and immunological separations involving monoclonal or polyclonal antibodies.

Based on the information contained in SEQ. ID. No. 1, the deduced full-length amino acid sequence for MTAse may be readily deduced. Using this information, MTAse and MTAse peptides may also be synthesized without undue experimentation by commonly used methods such as t-BOC or FMOC protection of alpha-amino groups. Both methods involve stepwise synthesis whereby a single amino acid is added at each step starting from the C terminus of the peptide (see, Coligan, et al., *Current Protocols in Immunology*, Wiley Interscience, 991, Unit 9). Peptides of the invention can also be synthesized by various well known solid phase peptide synthesis methods, such as those described by Merrifield, *J. Am. Chem. Soc.*, 85:2149 (1962), and Stewart and Young, *Solid Phase Peptides Synthesis*, (Freeman, San Francisco, 27–62, 1969), using a copoly(styrene-divinylbenzene) containing 0.1–1.0 mMol amines/g polymer.

In this latter method, completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

C. Production of Anti-MTAse Antibodies

The antigenicity of MTAse peptides can be determined by conventional techniques to determine the magnitude of the antibody response of an animal which has been immunized with the peptide. Generally, the MTAse peptides which are used to raise the anti-MTAse antibodies should generally be those which induce production of high titers of antibody with relatively high affinity for MTAse. Such peptides may be purified for use as immunogens using, for example, the method described in Rangione, et al., (*J. Biol. Chem.*, supra) or the methods for obtaining MTAse peptides described above.

Once antigenic peptides are prepared, antibodies to the immunizing peptide are produced by introducing peptide into a mammal (such as a rabbit, mouse or rat). For purposes of illustration, the amino acid sequences of two antigenic MTAse peptides are provided in the Sequence Listing appended hereto as SEQ ID. Nos. 2 and 3. Antibodies produced by rabbits immunized with these peptides showed a 50% maximal response to purified MTAse at, respectively, a 1:1500 and a 1:4000 dilution.

A multiple injection immunization protocol is preferred for use in immunizing animals with the antigenic MTAse peptides (see, e.g., Langone, et al., eds., "Production of Antisera with Small Doses of Immunogen: Multiple Intradermal Injections", *Methods of Enzymology* (Acad. Press, 1981). For example, a good antibody response can be obtained in rabbits by intradermal injection of 1 mg of the antigenic MTAse peptide emulsified in Complete Freund's Adjuvant followed several weeks later by one or more boosts of the same antigen in Incomplete Freund's Adjuvant.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because MTAse is presently believed to be conserved among mammalian species, use of a carrier protein to enhance the immunogenecity of MTAse proteins is preferred.

Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (see, for example, Coligan, et al., Unit 9, *Current Protocols in Immunology*, Wiley Interscience, 1991).

For preparation of monoclonal antibodies, immunization of a mouse or rat is preferred. The term "antibody" as used in this invention is meant also to include intact molecules as well as fragments thereof, such as for example, Fab and F(ab')$_2$, which are capable of binding the epitopic determinant. Also, in this context, the term "mAb's of the invention" refers to monoclonal antibodies with specificity for MTAse.

The general method used for production of hybridomas secreting monoclonal antibodies ("mAb's"), is well known (Kohler and Milstein, *Nature*, 256:495, 1975). Briefly, as described by Kohler and Milstein the technique comprised lymphocytes isolated from regional draining lymph nodes of five separate cancer patients with either melanoma, teratocarcinoma or cancer of the cervix, glioma or lung, were obtained from surgical specimens, pooled, and then fused with SHFP-1. Hybridomas were screened for production of antibody which bound to cancer cell lines.

Confirmation of MTAse specificity among mAb's can be accomplished using relatively routine screening techniques (such as the enzyme-linked immunosorvent assay, or "ELISA") to determine the elementary reaction pattern of the mAb of interest.

It is also possible to evaluate an mAb to determine whether it has the same specificity as a mAb of the invention without undue experimentation by determining whether the mAb being tested prevents a mAb of the invention from binding to MTAse isolated as described above. If the mAb being tested competes with the mAb of the invention, as shown by a decrease in binding by the mAb of the invention, then it is likely that the two monoclonal antibodies bind to the same or a closely related epitope.

Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

D. MTAse Detection Kits

MTAse detection kits may be prepared for use in laboratory and clinical settings which include reagents useful in the methods described above. For example, a kit for use in the method of Section A, supra, would preferably include oligonucleotide primers (produced as described in Section B above), detectably labelled hybridization probes and reagant coated microtiter plates. The kit could also include the antibodies described in Section C above for use in immunological detection of MTAse protein (as described in co-pending application, Ser. No. 08/176,413, filed Dec. 29, 1993.

The invention having been fully described, examples illustrating its practice are provided below. These examples should be considered as exemplars only and not as limiting the scope of the invention.

In the Examples, the following abbreviations are use: AS=anti-sense, DTT=dithiothreitol; min=minutes; MTAse= 5'-deoxy-5'-methylthioadenosine phosphorylase; PCR= polymerase chain reaction; S=sense; SSc=0.3 M NaCl, 0.03 M sodium citrate dehydrate; v/v=volume per volume; SDS= sodiumdodecyl sulfate.

EXAMPLE I

Test For MTAse Catalytic Activity in a Sample

The phosphorolysis activity of MTAse was determined by measuring the formation of [methyl-$^{14}$C] 5-methylthioribose-1-phosphate from [methyl-$^{14}$C]5'-deoxy-5'-methylithioadenosine (Seidenfeld et al. Biochem. Biophys. Res. Commun. 95, 1861–1866, 1980). In a total volume of 200 microliters the standard reaction mixture contained 50 mM potassium phosphate buffer, pH 7.4, 0.5 mM [methyl-$^{14}$C] 5'deoxy-5'-methylthioadenosine ($2\times10^5$ CPM/mmol), 1 mM DTT and the indicated amounts of enzyme. After incubation at 37° C. for 20 min, the reaction was stopped by addition of 50 microliters of 3 M trichloroacetic acid and 200 microliter aliquots were applied to a 0.6×2 cm column of "Dowex" 50-H* equilibrated with water. The [methyl-$^{14}$C] 5 methylthioribose-1-phosphate was eluted directly into scintillation vials containing 2 ml of −0.1 M HCl.

EXAMPLE II

Purification of Native MTAse from Rat Liver

MTAse was isolated from rat liver modifying the method of Rangione et al. (J. Biol. Chem. 261, 12324–12329, 1986). 50 g of fresh rat liver were homogenized in a Waring Blendor with 4 volumes of 10 mM potassium phosphate buffer, pH 7.4, containing 1 mM DTT (Buffer A). The homogenate was centrifuged (1 h at 15,000×g), and the resulting supernatant was subjected to ammonium sulfate fractionation. The precipitate between 55 and 75% saturation was collected by centrifugation (15,000×g for 20 min) and dissolved in a minimal volume of Buffer A. The sample was then dialyzed overnight against three changes of 100 volumes of the same buffer.

The sample was clarified by centrifugation at 15,000×g for 30 min and then applied to a DEAE-Sephacryl column (1.5×18 cm; Pharmacia) previously equilibrated with Buffer A. After washing with 80 ml of equilibration buffer, a linear gradient (80 ml) or 0–0.3 M NaCl in buffer A was applied. MTAse activity was eluted between 0.1 and 0.15 M NaCl. Fractions containing at least 0.06 units/mg of protein were concentrated 20-fold by ultrafiltration (Amicon PM-10 Diaflow membranes) and dialyzed expensively against 25 mM potassium phosphate buffer, pH 7.4 containing 1 mM DTT (Buffer B). The sample was then applied to a hydroxyapatite column (1×12 cm) (Bio-Rad). After elution of non-absorbed proteins with Buffer B, the column was washed with about 40 ml of 50 mM potassium phosphate buffer, pH 7.4, containing 1 mM DTT.

MTAse was then eluted using a linear gradient (40 ml) of 50–250 mm potassium phosphate, pH 7.4. Fractions containing MTAse activity were concentrated 30-fold by ultrafiltration and freed from dithiothreitol by repeated concentration and dilution with 50 mM potassium phosphate buffer, pH 7.4. The partially purified enzyme was then applied to a column (0.8×3 cm) of organomercurial agarose (Bio-Rad) equilibrated with 50 Mm phosphate buffer, pH 7.4. Elution of the column was carried out stepwise with a) 50 mM potassium phosphate buffer, pH 7.4; b) 50 mM potassium phosphate buffer, pH 7.4, 2 M KCl; and c) 50 mM potassium phosphate buffer, pH 7.4, 2 M KCl, 40 mM 2-mercaptoethanol. The enzyme was then eluted with 50 mM potassium phosphate buffer, pH 7.4, 2 M KCl, 200 mM 2-mercaptoethanol. Fractions containing at least 3 units/mg of protein were pooled, concentrated to 1 ml by ultrafiltration, and dialyzed overnight against 1000 volumes of 10 mM Tris/HCl, pH 7.4, 1 M DTT (Buffer C). As a final purification step, aliquots of the sample (1 ml) were injected at a flow rate of 1 ml/min into a "MONO Q" column (Pharmacia) pre-equilibrated with 10 mM Tris/HCl, pH 7.4, containing 1 mM DTT, and (0.5 ml fractions were collected. MTAse activity was eluted between 0.08 and 0.14 M NaCl in Buffer C. The fractions were concentrated to 0.5 ml by ultrafiltration and dialyzed against 1000 volumes of Buffer B.

EXAMPLE III

Determination of a Partial Amino Acid Sequence for Rat MTAse

The purified sample was lyophilized, dissolved in a 50 microliter sample loading buffer (1% sodium dodecylsulfate (SDS), 10% glycerin, 0.1 M DTT and 0.001% bromphenolblue) and loaded onto a 0.5 mm thick 10% SDS polyacrylamide gel (Bio Rad "MINIGEL" apparatus). After electrophoresis, proteins were electroblotted for 2 hr onto nitrocellulose (0.45 millimeter pore size, Millipore) in a Bio-Rad transblot system using transfer buffer (15 mM Tris, 192 mM glycine and 20% methanol, pH 8.3) as described by Towbin, et al. (*Proc. Nat'l Acad. Sci. USA* 76, 4340–4345, 1979).

After transfer, proteins were reversibly stained with Ponceau S (Sigma) using a modification of the method described by Salinovich and Montelaro (*Anal. Biochem.* 156, 341–347, 1987). The nitrocellulose filter was immersed for 60 sec in a solution of 0.1% Ponseau S dye in 1% aqueous acetic acid. Excess stain was removed from the blot by gentle agitation for 1–2 min in 1% aqueous acetic acid. The protein-containing region detected by stain was cut out, transferred to an Eppendorf tube (1.5 ml), washed with distilled water, and incubated for 30 min at 37° C. in 1.2 ml of 0.5% polyvinyl-pyrrolidone (average molecular weight= 40,000; PVP-40, Sigma) dissolved in 100 mM acetic acid in order to prevent absorption of the protease to the nitrocellulose during digestion. Excess PVP-40 was removed by extensive washing with water (at least five changes).

Nitrocellulose strips were then cut in small pieces of approximately 1 mm×1 mm and put back into the same tube. The protein on the nitrocellulose pieces was digested as described before (Los et al., *Science* 243:217–220, 1989). Trypsin (10 pmol) in 100 microliter of 100 mM Tris-HCl, pH 8.2/acetonitrile, 95;5 (v/v) is added and incubated at 37° C. overnight. After digestion, peptide-containing supernatant was acidified with 30 microliter of 10% trifluoroacetic acid, moved quickly on a Vortex, and centrifuged at 15,000×g for 1 min. The supernatant was removed and immediately injected into a reverse-phase HPLC system (Beckmann) equipped with a Brownlee Aquapore Bu-300 analytical column (2.1×100 mm).

Eluent D 0.1% trifluoroacetic acid (sequenal grade, in water) was pumped through the column for 5 min at a flow rate of 200 microliter/min before the flow was reduced to 100 microliter/min and the gradient is started with Eluent E (0.08–0.095% trifluoroacetic acid in acetonitrile/$H_2O$, 70;30 (v/v). Based on UV absorption at 215 nm peptide-containing fractions were collected manually into Eppendorf tubes. Representative fractions 60 and 77 were subjected to amino acid sequencing (ABl 477A Protein Sequencer with 120A Online PTH-AA Analyzer). Thus independent partial amino acid sequences of rat MTAse were obtained. The amino acid sequences of the peptides referred to as peptide 1 (fraction 60) and peptide 2 (fraction 77) are depicted in SEQ ID Nos. 5 to 6.

EXAMPLE IV

Amplication of a DNA Fragment Encoding Part of the Human MTAse Gene

Based on the partial amino acid sequences of peptides 1 (SEQ. ID. No. 4) and 2 (SEQ. ID. No. 5) two sets of oligonucleotide primers with different polarities were synthesized. Each oligonucleotide was designed to include a unique restriction site at its 5'-end (EcoRI or BamHI) in order to facilitate the subsequent cloning of the amplified DNA fragment. For use in PCR amplification total cDNA was isolated from 1 million plaque-forming-units (pfu) of human placenta cDNA gene library (Clontech) using the "Lambda-TRAP" kit (Clontech). The PCR reaction was carried out in a total volume of 100 microliters containing 1 microgram of total cDNA from human placenta cDNA gene library, 1×PCR buffer (10 mM KCl, 10 mM Tris-HCl, pH 8.3, 2.5 mM $MgCl_2$), 0.2 mM of each dNTP, 100 mg each of sense and anti-sense primers and 10 units of Taq DNA polymerase, Stoffel Fragment ("AMPLI TAQ", Perkin-Elmer Cetus).

Forty cycles were performed with the "GENE AMP" PCR System 9600 (Perkin-Elmer Cetus), each cycle consisting of denaturation (92° C., 1 min), annealing (55° C., 2 min) and extension (72° C., 2 min). The PCR product was separated electrophoretically on a 0.8% agarose gel in 1×TA buffer (40 mM Tris-acetate, 20 mM Na-acetate, 2 mM EDTA, pH 7.9) and a 450 bp DNA fragment was amplified. The PCR amplification product was double digested with restriction enzymes EcoRI/BamHI, separated on a 0.8% agarose gel in 1×TA buffer, recovered from the gel using "GENE CLEAN" Kit (Bio101), subcloned into EcoRI/BamHI cut pBluescript vector SK+ (Stratagene) and sequenced by the dideoxytermination method using universal sequencing primer ("SEQUENASE" Version 1.0 DNA sequencing kit USB).

EXAMPLE V

Screening of a Human Placenta cDNA Gene Library

Sequence analysis of the PCR amplified product (Example IV) shows perfect coincidence with the C-terminal amino acid sequence of peptide 1 (SEQ. ID No. 5). Using the 450 bp DNA fragment as hybridizaion probe, a human placenta cDNA gene library (Clontech) was screened. To that end, E. coli strain Y1090 host cells were incubated overnight with vigorous shaking at 37° C. in LB medium (per liter: 10 g tryptone, 5 g yeast extract, 10 g NaCl) containing 0.2% maltose and 10 mM MgSP. For each culture plate, 0.3 ml of host cell culture was mixed with $3×10^4$ pfu phage and incubated for 20 min at 37° C. The mixtures of host cells and phage were added to 8 ml of LB-medium containing 0.7% agarose (LB-top-agarose) that were pre-warmed at 48° C. and poured onto 20 agar plates (135×15 mm). Plaques were visible after incubation for 6 to 8 h at 37° C. and plates were chilled to 4° C. for 1 h. Plaques were transferred to Colony/Plaque Screen nylon transfer membranes (NEN Research Products, Dupont Boston, Ma.) for 3 min, followed by denaturation (2 times in 0.5 N NaOH for 2 min), renaturation (2 times in 1.0 M Tris-HCl, pH7.5 for 2 min) and fixation by air drying. Prehybridization of 20 membranes was carried out in two plastic bags containing 10 membranes each, using 20 ml of prehybridization buffer (1% SDS, 2×SSC, 10% dextran sulphate, 50% deionized formamide) for 4 h at 42° C.

The 450 bp EcoRI-BamHI fragment of the partial human MTAse gene was labeled with [alpha-$_{32}$P]dATP (3,000 Ci/mmol) using a nicktranslation kit (Boehringer Mannheim), separated from unincorporated radioactivity on a NICK-column (Pharmacia), denatured by heating at 96° C. for 10 min, chilled on ice and added to the membranes in the plastic bags with the probe concentration being 106 dpm/ml. The specific activity of the labeled probe is around $10^8$ dpm/microgram. Hybridization was performed overnight at 42° C. After hybridization, membranes were washed at room temperature three times for 5 min with excess of 2×SSC, then at 65° C. for 20 min with 2×SSC, 0.1% SDS and once at room temperature for 20 min with 0.2×SSC, 0.1% SDS. The washed membranes were exposed to an X-ray film overnight.

The agar plugs containing several plaques around a positive signal were removed into a 1 ml sterile phage diluent (50 mM Tris-HC1, pH 7.5, 0.1 M NaC1, 8 mM $MgSO_4$, 0.01% gelatine) and rescreened as above mentioned, until the pure positive plaques were obtained. From screening of approximately half a million plaques, 6 independent positive clones were obtained. After amplification on LB plates, each phage DNA of positive clones was purified using a "Lambda-TRAP" kit (Clontech). Purified phage DNAs were cut with EcoRI enzyme to obtain the whole insert, but because of the existence of an EcoRI site inside of the insert, two bands were cut out from all the clones.

Two EcoRI insert fragments (850 bp and 1100 bp) from the representative phage clone, designated as MTAp-1, were subcloned into EcoRI-cut pBluescript SK+ vector (Stratagene). These subclones were designated MTAP-2 (850 bp) and MTAP-3 (1100 bp), respectively. Restriction analysis and DNA sequencing of these two subclones reveal that subclone MTAP-2 has an open reading frame coding for 254 amino acids comprising the amino acid sequence corresponding to peptide 3 at its C-terminus (homology 90%). Calculated from the molecular weight of human MTAse of 32 kDa (F. D. Rangione et al., J. Bio. Chem. 261:12324–12329, 1986), it covers over 85% of total protein. About 50 amino acids (at least 150 bp on DNA level) are missing.

EXAMPLE VI

Primer Extension to Obtain the Missing 5' End cDNA of MTAse

To obtain the 5'-terminal missing DNA fragment, RACE (rapid amplification of cDNA ends) was applied (Loh et al., Science 243:217–220, 1989; Frohman, et al. PNAS 85:8998–9002, 1988). One microgram of poly (A+) RNA from human placenta (Clontech) in 6.25 microliters of $H_2O$ was heated at 65° C. for 5 min, quenched on ice, and added to 4 microliters of 5×RTC buffer (250 mM Tris-HC1, pH 8.15, 30 mM $MgCl_2$, 200 mM KCl, 5 mM DTT), 4 microliters (0.4 mg/ml) of actinomycin D (Boehringer), 1 microliters of each dNTP (20 mM), 0.25 microliters (10 units) of RNasin (Boehringer), 1 microliter of [alpha-$^{35}$S] dATP (1443 Ci/mmol), 1 microliter of human MTAse specific anti-sense oligonucleotide 3 AS and 10 units of avian myeloblastosis virus reverse transcriptase (Boehringer). The mixture was incubated for 2 hr at 42° C.

Excess primer and dNTPs were removed as follows; the 20 microliter cDNA pool was applied to a NICK-column (Pharmacia) and two-drop fractions were collected. Fractions 5–8 relative to the first peak of radioactivity were pooled, precipitated with 1/10 volume of 7.5 M NHOAc and 2.5 volume of ethanol at −80° C. for 2 hr, centrifuged at 15,000×g for 30 min at 4° C., washed with 0.5 ml of 80% ethanol, dried under reduced pressure (Speedvac) and dissolved in 20 microliter of H$_2$O. For tailing, 1.5 microliter of dGTP (20 mM), 2.4 microliter of CoCll$^2$ (25 mM), 6 microliter of 5×tailing buffer (1 mM potassium cacodylate, 125 mM Tris-HCl, pH 6.6, 1.25 mg/ml bovine serum albumin) and 0.5 microliter of (15 units) terminal deoxynucleotidyl transferase (Boehringer) were added.

The mixture was incubated for 1 hr at 37° C., heated for 15 min at 65° C., extracted once with the same volume of TE-buffer (10 mM Tris-HCl, pH 7.5, 0.1 mM EDTA) saturated with phenol, and then precipitated with ethanol as mentioned above. The tailed cDNA pool was dissolved in 20 microliter of H$^O$ and 1 microliter was used for PCR. For amplification two additional primers were synthesized. One primer was a MTAse specific anti-sense primer which locates 180 bp upstream of the position of oligonucleotide 3AS. The other was a primer for the poly(G) end. Amplification was performed for 40 cycles as described above. Each cycle consisted of denaturation (92° C., 1 min), annealing (50° C., 2 min) and extension (72° C., 0.5 min).

The PCR product was separated electrophoretically on a 0.8% agarose gel. The obtained 520 bp DNA fragment was specifically amplified. After purification on a 0.8% agarose preparative gel, the 520 bp DNA fragment was digested with Not I and Bcl I (the relevant restriction sites being present in the overlapping domain between the extended DNA fragment and the original fragment of subclone MTAP-2) and subcloned into Not I/BamHI-cut pBluescript SK$^+$ vector (Stratagene). Sequence analysis of three independent subclones, designated MTAP-4, MTAP-5 and MTAP-6, respectively, revealed that each of these clones contains an exactly matched amino acid sequence in the overlapping domain.

The lengths of these three primer-extended cDNA subclones are slightly different. This implies that they are independent PCR products and that their sequences reflect the correct mRNA sequence without any base mid-incorporation during PCR amplification. The combination of the new upstream sequence with the start codon ATG (coding for methionine) and the downstream sequence from subclone MTA-2 generates an open reading frame coding for 283 amino acids.

EXAMPLE VII

Expression of Recombinant Human MTAse in *E. Coli*

The full-length cDNA of human MTAse was constructed by adding the primer-extended cDNA fragment of subclone MTAP-4, which contains the largest insert of the three subclones obtained in Example VI, to the 5'end of the DNA insert of subclone MTAP-2 using their common restriction site Hindll. The Not I/Hindll-DNA fragment from subclone MTAP-4 and the large Hindll/EcoRI fragment from subclone MTAP-2 were mixed and subcloned into Not I/EcoRI-cut pBluescript vector SK$^+$ (Stratagene). The obtained subclone containing a full-length cDNA of human MTAse was designated MTAP-7. To check the authenticity of this cDNA clone, the recombinant protein was expressed using *E. coli* expression vector pKK223-3 equipped with the Taq promotor (Pharmacia).

To generate a new site EcoRI-site at the 5'end and a Pst I site at 3'-end of the cDNA fragment, PCR was used applying a 5'-primer oligonucleotide comprising the Shine-Dalgarno (SD) sequence and another 3'-primer. Amplification was performed for 20 cycles as mentioned above with each cycle consisting of denaturation (92° C., 1 min), annealing (55° C., 1 min) and extension (72° C., 1 min). The PCR product was digested with restriction enzymes EcoRI/Pst I, purified electrophoretically on a 0.8% agarose gel and subcloned into EcoRI/PstI-cut pBluescript vector SK$^+$ (Stratagene).

After checking the full sequence of the insert in the subclone referred to as MTAP-8, the EcoRI/Pst I fragment was cut out and subcloned into EcoRI/Pst I cut pKK223-3 vector yielding human MTAse cDNA in an *E. coli* expression vector. The subclone designated as MTAP-9 was transformed into *E. coli* strain JM105. The enzymatic activity and the spectrum of total proteins of transformed cells with and without isopropyl-beta-D-thiogalactopyranoside (IPTG) induction were analyzed. A singe transformed colony was inoculated into 2 ml of LB medium and incubated overnight at 37° C., 20 microliter of this overnight culture are added into two plastic tubes, each containing fresh 2 ml of LB medium (1/100 dilution).

After incubation at 37° C. for 1 hr to one tube 20 microliter of 0.1 M IPTG added for induction to give a final concentration of 1 mM IPTG and incubated at 37° C. for additional 4 hr. After harvesting the cells by centrifugation at 15,000×g for 5 min, the cells were resuspended in 100 microliters of phosphate buffer (50 mM potassium phosphate, pH 7.5, 1 mM DTT), disrupted by sonication on ice at step 3 for 0.5 min and crude cell extracts are obtained by centrifugation at 15,000×g for 10 min.

The protein concentration was determined using the Bradford method (Bio-Rad, Protein Assay). The same amounts of samples with and without IPTG induction were analyzed for enzymatic activity and subjected to electrophoresis on a 10% SDS polyacrylamide gel. The crude extract obtained from IPTG induced cells displayed an MTAse activity which is more than 5-fold higher than that of non-induced cells. Furthermore, on the SDS gel a new induced protein band (31 kDa) was detected.

EXAMPLE VIII

Cloning and Partial Characterization of the MTAse Genomic Clone

For the most efficient amplification of DNA fragment by PCR for diagnostic purposes, its size should preferably be less than 500 bp. The cDNA sequence reflects the sum of exons, which are normally separated by introns which makes it difficult to find out an adequate sequence with appropriate size from the cDNA sequence. To overcome this problem, a genomic clone of human MTAse was isolated. A cosmid gene library constructed from human placenta DNA (Clontech) was screened using MTAse cDNA gene probe, the Not I/EcoRI fragment from subclone MTAP-7. Transformed *E. coli* cells from the library are plated on LB plates containing ampicillin (50 mg/l) with a colony density of 1–2×10⁴/135×15 mm plate.

The following procedures were performed as described in Example IV. From half a million colonies, a single positive colony designated as MTAP-10 was isolated and partially characterized by PCR analysis and by direct sequencing. Two primers, a sense oligonucleotide located 120 bp upstream of the stop codon and an anti-sense oligonucleotide located 20 bp downstream of the stop codon were synthesized and used for PCR analysis. PCR was performed for 25 cycles, each cycle consisting of denaturation (92° C., 1 min), annealing (55° C., 2 min) and extension (72° C., 5 min). The PCR products were separated on a 0.8% agarose gel.

The location of exons identified to date in the MTAse gene using the above-described technique is depicted in FIG. 1.

EXAMPLE IX

Application of MTAse Sequence-Specific Oligonucleotides to Malignant Cell Lines to Detect the Presence or Absence of MTAse Therein To test the usefulness of oligonucleotides PCR was applied for several cell lines which were known to contain MTAse positive and negative cells. Genomic DNAs were isolated as described in Example VIII and 1 microgram thereof was used for PCR. Amplification was performed for 40 cycles as described above, with each cycle consisting of denaturation (92° C., 1 min), annealing (55° C., 1 min), and extension (72° C., ½ min). The PCR products were analyzed on a 1.5% agarose gel. No MTAse was detected in cell lines which were known to be MTAse negative, while MTAse was detected in the MTAse positive cell lines.

SUMMARY OF SEQUENCES

SEQUENCE ID. NO. 1 is a genomic clone for methylthioadenosine phosphorylase (MTAse).

SEQUENCE ID. NO. 2 is an antigenic MTAse peptide ("peptide 40").

SEQUENCE ID. NO. 3 is an antigenic MTAse peptide ("peptide 51").

SEQUENCE ID. NO. 4 is a peptide amino acid sequence deduced from the oligonucleotide sequence of a primer for PCR amplification of the gene for MTAse ("peptide 1").

SEQUENCE ID. NO. 5 is a peptide amino acid sequence deduced from the oligonucleotide sequence of a primer for PCR amplification of the gene for MTAse ("peptide 2").

We claim:

1. A method for detecting the presence of catalytically active and catalytically inactive methylthioadenosine phosphorylase (MTAse) in mammalian cells comprising:
   (a) obtaining an assayable sample of cells which are suspected of being MTAse deficient,
   (b) adding oligonucleotide probes which will specifically hybridize to any of the MTAse encoding nucleic acid present in the sample under conditions which will allow the probes to detectably hybridize to any such nucleic acid present in the sample, and
   (c) detecting whether the MTAse encoding nucleic acid is present in the sample, wherein the presence of said nucleic acid is indicative of the presence of catalytically active or inactive MTAse in a cell.

2. A method according to claim 1 comprising further the step of subjecting the sample to conditions favoring the selective amplification of a nucleic acid which will encode for MTAse and selectively amplifying any MTAse encoding nucleic acid present in the sample.

3. A method according to claim 1 wherein the cells are derived from a known malignancy.

4. A method according to claim 3 wherein the cells are also assayed for MTAse catalytic activity.

5. A method according to claim 2 wherein the conditions employed comprise a polymerase chain reaction.

6. An isolated polynucleotide which encodes MTAse having the nucleic acid sequence shown in the Sequence Listing appended hereto as SEQ. ID. No. 1.

7. A recombinant expression vector containing the polynucleotide of claim 6.

8. An isolated polynucleotide according to claim 6 comprising only the exon coding regions of the nucleic acid sequence shown in FIG. 1.

9. A recombinant expression vector containing the polynucleotide of claim 8.

* * * * *

UNITED STATES PATENT AND TRADEMARK OFFICE
CERTIFICATE OF CORRECTION

PATENT NO.   : 5,942,393
DATED        : August 24, 1999
INVENTOR(S)  : Tsutomu Nobori, Dennis A. Carson and Kenji Takabayashi It is certified that error appears in the above-identified patent and that said Letters Patent is hereby corrected as shown below:

Title page,
Delete "1 Drawing Sheet" and substitute therefor -- 2 Drawing Sheets --; and Drawings,
Insert Sheet 1 of 2 and Sheet 2 of 2, as shown on the attached pages Signed and Sealed this Twenty-second Day of July, 2003

JAMES E. ROGAN
*Director of the United States Patent and Trademark Office*

```
   1  TTTATACAGA GCATGACAGT GGGGTCCTCA CTAGGGTCTG TCTGCCACTC
  51  TACATATTTG AAACAGGAGT GGCTTCTCAG AATCCAGTGA ACCTAAATTT
 101  TAGTTTTAGT TGCTCACTGG ACTGGGTTCT AGGAGACCCC CTGTGTTAGT
 151  CTGTGGTCAT TGCTAGSAGA ATCACTTAAT TTTTTCTAGA CTCTAGGAGA
 201  AAACAGTTGG TGGTGTACTC ATCACGGGTT AACAATTTCT TCTCTCCTTC
 251  CATAGGCATG GAAGGCAGCA CACCATCATG CCTTCAAAGG TCAACTACCA
 301  GGCGAACATC TGGGCTTTGA AGGAAGAGGG CTGTACACAT GTCATAGTGA
 351  CCACAGCTTG TGGCTCCTTG AGGGAGGAGA TTCAGCCCGG CGATATTGTC
 401  ATTATTGATC AGTTCATTGA CANNNNNNNN NNNNNNNNNN GAGGTCGACG
 451  GTATCGATAA GCTTTGTAAA CAATTGTCTT TAGCTTATCC AGAGGAATTG
 501  AGTCTGGAGT AAAGACCCAA ATATTGACCT AGATAAAGTT GACTCACCAG
 551  CCCTCGGAGG ATGGAAAGAT GGCCTTAAAA TAAAACAAAC AAAAACCTTT
 601  TTGCTTTAT TTTGTAGGAC CACTATGAGA CCTCAGTCCT TCTATGATGG
 651  AAGTCATTCT TGTGCCAGAG GAGTGTGCCA TATTCCAATG GCTGAGCCGT
 701  TTTGCCCCAA AACGAGAGAG GTGTGTAGTC TTTCTGGAAG GTGTACCAGA
 751  ATAAATCATG TGGGCTTGGG GTGGCATCTG GCATTTGGTT AATTGGCAGA
 801  CGGAGTGGCC CCATACCCTC ACTCAAGTTT GCTTTGTATT ATGCAAGTTT
 851  ATGGAGAGTT ATTTCCTGTT GCTAATAATT TNNNNNNNNN NNNNNNNNNN
 901  AAGTGCAGCC TTAAGTTGTG CATGTGCTAG TATGTTTTGA AGTTTCTGGT
 951  TTTTCTTTTC TAGGTTCTTA TAGAGACTGC TAAGAAGCTA GGACTCCGGT
1001  GCCACTCAAA GGGGACAATG GTCACAATCG AGGGACCTCG TTTTAGCTCC
1051  CGGGCAGAAA GCTTCATGTT CCGCACCTGG GGGCGGATG TTATCAACAT
1101  GACCACAGTT CCAGAGGTGG TTCTTGCTAA GGAGGCTGGA ATTTGTTACG
1151  CAAGTATCGC CATGGGCACA GATTATGACT GCTGGAAGGA GCACGAGGAA
1201  GCAGTAGGTG GAATTCTTTT CTAAGCACAT ATAGCATGGG TTTCTGGGTG
1251  CCAATAGGGT GTCTTAACTG TTTGTTTCTA TTACGTTAGT TTCAGAAAGT
1301  GCCTTTCTAC AAGGTTTTGA AGTTGTTAAT ATTTTCTGTA GTTCCATTGG
1351  AAGGTAAGAA CAAAGATCAA AAGAAAGAAA GAGACACTTT TACCCAAGGA
1401  TCAGTAGTGA AAATAGTACA TTGTAGGCAT GTAGATGTGT TGAGAATCAT
```

FIGURE 1

```
1451  ACTAAGACTT GGGCCTTANN NNNNNNNNNN NNNNNNNNNN NNTACCCTAC
1501  ATTGAGGATT CGGTTTCAGC AGATAAATTT GAGGGACACA AACATTTAGG
1551  CTGTAGCAAG GCTGGAGCTC AGAAAAATGT TTTATGACAA GCAGTGGAAT
1601  TTTAAGTTCT AGTAACCTCC AGTGCTATTG TTTCTCTAGG TTTCGGTGGA
1651  CCGGGTCTTA AAGACCCTGA AAGAAAACGC TAATAAAGCC AAAAGCTTAC
1701  TGCTCACTAC CATACCTCAG ATAGGGTCCA CAGAATGGTC AGAAACCCTC
1751  CATAACCTGA AGGTAAGTGC AGCCATGGAC AATCAGGCAT GTCTGTAGAC
1801  TCTCTATTGT CTTCTTTTCT TACTTGCATT TCACCTTTGG TCCTCATGTA
1851  TTTTTTGCCA GCCTAGATGT TTTCAACAAG TTTTTGTGAC ATCTACTACT
1901  ACCATACCAA CCACTTGTGA AACTGAGTAG TCTTATTTTC TTGGCTGGTA
1951  GTGCAGANNN NNNNNNNNNN NNAATAAACA ATAATCCAGG CTGGGCTGGT
2001  ATGGCAATAA GTGATTATCA GAACAATGCT CTGAGATAAG CATTATTAAC
2051  CTCACTTTAC AGGAAAGGGA GGTGAGGAAC AAGAGTTTA GAGTACCCGA
2101  AGTTCCACAT CTGGTTAGTG AACTTGAAAA TTTTCTGTAG AATTTATTTA
2151  AAGTGTATGT TTCCTGCGTC CTCACTTTGA TCTAGAAAAT CAAAATCTGT
2201  TTTTTTTTTT AACAAACATC TCAGTAATTA CGCCAACATG TGAATATCAC
2251  TGCCTCCTTT CTTCCTTTCA GAATATGGCC CAGTTTTCTG TTTTATTACC
2301  AAGACATTAA AGTAGCATGG CTGCCCAGGA GAAAAGAAGA CATTCTAATT
2351  CCAGTCATTT TGGGAATTCC TGCTTAACTT GAAAAAAATA TGGGAAAGAC
2401  ATGCAGCTTT CATGCCCTTG CCTATCAAAG AGTATGTTGT AAGAAAGACA
2451  AGACATTGTG TGTATAGAGA CTCCTCAATG ATTTAGACAA CTTCAAAATA
2501  CAGAAGAAAA GCAAATGACT AGTAACATGT GGGAAAAAAT ATTACATTTT
2551  AAGGGGGAAA AAAAACCCCA CCATTCTCTT CTCCCCCTAT TAAATTTGCA
2601  ACAATAAAGG GTGGAGGGTA ATCTCTACTT TCCTATACTG CCAAAGAATG
2651  TGAGGAAGAA ATGGGACTCT TTGGTTATTT ATTGATGCGA CTGTAAATTG
2701  GTACAGTATT TCTGGAGGGC AATTTGGTAA AATGCATCAA AAGACTTAAA
2751  AATACGGACG TAC
```

Figure. The genomic sequence of MTAP gene. Exons are underlined.

FIGURE 1

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2763 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: methyladenosine phosphatase (ix) FEATURE:
      (A) NAME/KEY: CDS
      (B) LOCATION: 1..2763

(xi) SEQUENCE DESCRIPTION: SEQ ID NO:1:

```
TTTATACAGA GCATGACAGT GGGGTCCTCA CTAGGGTCTG TCTGCCACTC TACATATTTG      60

AAACAGGAGT GGCTTCTCAG AATCCAGTGA ACCTAAATTT TAGTTTTAGT TGCTCACTGG     120

ACTGGGTTCT AGGAGACCCC CTGTGTTAGT CTGTGGTCAT TGCTAGSAGA ATCACTTAAT     180

TTTTTCTAGA CTCTAGGAGA AAACAGTTGG TGGTGTACTC ATCACGGGTT AACAATTTCT     240

TCTCTCCTTC CATAGGCATG GAAGGCAGCA CACCATCATG CCTTCAAAGG TCAACTACCA     300

GGCGAACATC TGGGCTTTGA AGGAAGAGGG CTGTACACAT GTCATAGTGA CCACAGCTTG     360

TGGCTCCTTG AGGGAGGAGA TTCAGCCCGG CGATATTGTC ATTATTGATC AGTTCATTGA     420

CANNNNNNNN NNNNNNNNNN GAGGTCGACG GTATCGATAA GCTTTGTAAA CAATTGTCTT     480

TAGCTTATCC AGAGGAATTG AGTCTGGAGT AAAGACCCAA ATATTGACCT AGATAAAGTT     540

GACTCACCAG CCCTCGGAGG ATGGAAAGAT GGCCTTAAAA TAAAACAAAC AAAAACCTTT     600
```

-continued

| | | | | |
|---|---|---|---|---|
| TTTGCTTTAT | TTTGTAGGAC | CACTATGAGA | CCTCAGTCCT | TCTATGATGG AAGTCATTCT 660 |
| TGTGCCAGAG | GAGTGTGCCA | TATTCCAATG | GCTGAGCCGT | TTTGCCCCAA AACGAGAGAG 720 |
| GTGTGTAGTC | TTTCTGGAAG | GTGTACCAGA | ATAAATCATG | TGGGCTTGGG GTGGCATCTG 780 |
| GCATTTGGTT | AATTGGCAGA | CGGAGTGGCC | CCATACCCTC | ACTCAAGTTT GCTTTGTATT 840 |
| ATGCAAGTTT | ATGGAGAGTT | ATTTCCTGTT | GCTAATAATT | TNNNNNNNNN NNNNNNNNNN 900 |
| AAGTGCAGCC | TTAAGTTGTG | CATGTGCTAG | TATGTTTTGA | AGTTTCTGGT TTTTCTTTTC 960 |
| TAGGTTCTTA | TAGAGACTGC | TAAGAAGCTA | GGACTCCGGT | GCCACTCAAA GGGGACAATG 1020 |
| GTCACAATCG | AGGGACCTCG | TTTTAGCTCC | CGGGCAGAAA | GCTTCATGTT CCGCACCTGG 1080 |
| GGGGCGGATG | TTATCAACAT | GACCACAGTT | CCAGAGGTGG | TTCTTGCTAA GGAGGCTGGA 1140 |
| ATTTGTTACG | CAAGTATCGC | CATGGGCACA | GATTATGACT | GCTGGAAGGA GCACGAGGAA 1200 |
| GCAGTAGGTG | GAATTCTTTT | CTAAGCACAT | ATAGCATGGG | TTTCTGGGTG CCAATAGGGT 1260 |
| GTCTTAACTG | TTTGTTTCTA | TTACGTTAGT | TTCAGAAAGT | GCCTTTCTAC AAGGTTTTGA 1320 |
| AGTTGTTAAT | ATTTTCTGTA | GTTCCATTGG | AAGGTAAGAA | CAAAGATCAA AAGAAAGAAA 1380 |
| GAGACACTTT | TACCCAAGGA | TCAGTAGTGA | AAATAGTACA | TTGTAGGCAT GTAGATGTGT 1440 |
| TGAGAATCAT | ACTAAGACTT | GGGCCTTANN | NNNNNNNNNN | NNNNNNNNNN NNTACCCTAC 1500 |
| ATTGAGGATT | CGGTTTCAGC | AGATAAATTT | GAGGGACACA | AACATTTAGG CTGTAGCAAG 1560 |
| GCTGGAGCTC | AGAAAAATGT | TTTATGACAA | GCAGTGGAAT | TTTAAGTTCT AGTAACCTCC 1620 |
| AGTGCTATTG | TTTCTCTAGG | TTTCGGTGGA | CCGGGTCTTA | AAGACCCTGA AGAAAACGC 1680 |
| TAATAAAGCC | AAAAGCTTAC | TGCTCACTAC | CATACCTCAG | ATAGGGTCCA CAGAATGGTC 1740 |
| AGAAACCCTC | CATAACCTGA | AGGTAAGTGC | AGCCATGGAC | AATCAGGCAT GTCTGTAGAC 1800 |
| TCTCTATTGT | CTTCTTTTCT | TACTTGCATT | TCACCTTTGG | TCCTCATGTA TTTTTTGCCA 1860 |
| GCCTAGATGT | TTTCAACAAG | TTTTTGTGAC | ATCTACTACT | ACCATACCAA CCACTTGTGA 1920 |
| AACTGAGTAG | TCTTATTTTC | TTGGCTGGTA | GTGCAGANNN | NNNNNNNNNN NNAATAAACA 1980 |
| ATAATCCAGG | CTGGGCTGGT | ATGGCAATAA | GTGATTATCA | GAACAATGCT CTGAGATAAG 2040 |
| CATTATTAAC | CTCACTTTAC | AGGAAAGGGA | GGTGAGGAAC | CAAGAGTTTA GAGTACCCGA 2100 |
| AGTTCCACAT | CTGGTTAGTG | AACTTGAAAA | TTTTCTGTAG | AATTTATTTA AAGTGTATGT 2160 |
| TTCCTGCGTC | CTCACTTTGA | TCTAGAAAAT | CAAAATCTGT | TTTTTTTTTT AACAAACATC 2220 |
| TCAGTAATTA | CGCCAACATG | TGAATATCAC | TGCCTCCTTT | CTTCCTTTCA GAATATGGCC 2280 |
| CAGTTTTCTG | TTTTATTACC | AAGACATTAA | AGTAGCATGG | CTGCCCAGGA GAAAAGAAGA 2340 |
| CATTCTAATT | CCAGTCATTT | TGGGAATTCC | TGCTTAACTT | GAAAAAAATA TGGGAAAGAC 2400 |
| ATGCAGCTTT | CATGCCCTTG | CCTATCAAAG | AGTATGTTGT | AAGAAAGACA AGACATTGTG 2460 |
| TGTATAGAGA | CTCCTCAATG | ATTTAGACAA | CTTCAAAATA | CAGAAGAAAA GCAAATGACT 2520 |
| AGTAACATGT | GGGAAAAAAT | ATTACATTTT | AAGGGGAAA | AAAAACCCCA CCATTCTCTT 2580 |
| CTCCCCCTAT | TAAATTTGCA | ACAATAAAGG | GTGGAGGGTA | ATCTCTACTT TCCTATACTG 2640 |
| CCAAAGAATG | TGAGGAAGAA | ATGGGACTCT | TTGGTTATTT | ATTGATGCGA CTGTAAATTG 2700 |
| GTACAGTATT | TCTGGAGGGC | AATTTGGTAA | AATGCATCAA | AAGACTTAAA AATACGGACG 2760 |
| TAC | | | | 2763 |

(2) INFORMATION FOR SEQ ID NO:2:

(i) SEQUENCE CHARACTERISTICS:
      (A) LENGTH: 17 amino acids
      (B) TYPE: amino acid -continued

```
            (C) STRANDEDNESS: single
            (D) TOPOLOGY: linear (ii) MOLECULE TYPE: peptide (vii) IMMEDIATE SOURCE:
            (B) CLONE: methyladenosine phosphatase peptides (ix) FEATURE:
            (A) NAME/KEY: Peptide
            (B) LOCATION: 1..17

(xi) SEQUENCE DESCRIPTION: SEQ ID NO:2:

Ile Gly Ile Ile Gly Gly Thr Gly Leu Asp Asp Pro Glu Ile Leu Glu
1               5                  10                 15

Gly (2) INFORMATION FOR SEQ ID NO:3:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: methyladenosine phosphatase peptides (ix) FEATURE:
            (A) NAME/KEY: Peptide
            (B) LOCATION: 1..13

(xi) SEQUENCE DESCRIPTION: SEQ ID NO:3:

Leu Leu Leu Thr Thr Ile Pro Gln Ile Gly Ser Met Glu
1               5                  10

(2) INFORMATION FOR SEQ ID NO:4:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: methyladenosine phosphatase primers (ix) FEATURE:
            (A) NAME/KEY: Peptide
            (B) LOCATION: 1..8

(xi) SEQUENCE DESCRIPTION: SEQ ID NO:4:

Tyr Val Asp Thr Pro Phe Gly Lys
1               5

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: methyladenosine phosphatase primers
```

-continued

```
(ix) FEATURE:
    (A) NAME/KEY: Peptide
    (B) LOCATION: 1..9

(xi) SEQUENCE DESCRIPTION: SEQ ID NO:5:

Thr Trp Gly Ala Asp Val Ile Asn Met
1               5
```